(12) United States Patent
Figaro

(10) Patent No.: US 9,863,867 B2
(45) Date of Patent: Jan. 9, 2018

(54) AUTOMATICALLY UPDATING HARD IRON AND SOFT IRON COEFFICIENTS OF A MAGNETIC SENSOR

(71) Applicant: Davy J. Figaro, Sebastopol, CA (US)

(72) Inventor: Davy J. Figaro, Sebastopol, CA (US)

(73) Assignee: PNI Sensor Corporation, Santa Rosa, CA (US)

( * ) Notice: Subject to any disclaimer, the term of this patent is extended or adjusted under 35 U.S.C. 154(b) by 381 days.

(21) Appl. No.: 14/628,259

(22) Filed: Feb. 22, 2015

(65) Prior Publication Data

US 2015/0241390 A1    Aug. 27, 2015

Related U.S. Application Data

(60) Provisional application No. 61/943,413, filed on Feb. 23, 2014.

(51) Int. Cl.
*G01R 33/02* (2006.01)
*G01N 19/00* (2006.01)
*G01C 17/38* (2006.01)
*G01R 33/00* (2006.01)

(52) U.S. Cl.
CPC .............. *G01N 19/00* (2013.01); *G01C 17/38* (2013.01); *G01R 33/0035* (2013.01); *G01R 33/0064* (2013.01)

(58) Field of Classification Search
None
See application file for complete search history.

(56) References Cited

U.S. PATENT DOCUMENTS

| | | | |
|---|---|---|---|
| 7,451,549 B1 | 11/2008 | Sodhi et al. | |
| 7,826,999 B1 | 11/2010 | Boeen et al. | |
| 7,844,415 B1 * | 11/2010 | Bryant | G01C 17/02 702/141 |
| 7,930,148 B1 | 4/2011 | Figaro et al. | |
| 8,032,324 B1 * | 10/2011 | Bryant | G01C 17/02 702/141 |
| 8,121,812 B2 * | 2/2012 | Higgins | A61B 5/06 324/207.17 |
| 8,140,285 B2 * | 3/2012 | Reene | G01C 17/38 33/333 |
| 8,223,121 B2 * | 7/2012 | Shaw | G06F 3/017 345/158 |
| 8,464,433 B1 * | 6/2013 | Cardarelli | G01C 19/38 33/318 |

(Continued)

*Primary Examiner* — Michael Lebentritt
(74) *Attorney, Agent, or Firm* — Brian R. Short

(57) ABSTRACT

Apparatuses, methods and systems apparatus for automatically updating hard iron and soft iron coefficients of a magnetic sensor of a device are disclosed. One method includes making measurements of a magnetic field by the magnetic sensor during rotations of the device, determining by at least a criterion whether to input the measurements of the magnetic field into a coefficient estimator, calculating, by the coefficient estimator, new hard iron and soft iron coefficients upon receiving the measurements of the magnetic field, determining a quality of the newly calculated hard iron and soft iron calculated coefficients, and updating existing hard iron and soft iron coefficients to the newly calculated hard iron and soft iron coefficients only if the quality of the newly calculated hard iron and soft iron coefficients.

18 Claims, 6 Drawing Sheets

(56) References Cited

U.S. PATENT DOCUMENTS

| | | | | |
|---|---|---|---|---|
| 8,515,707 | B2 * | 8/2013 | Joseph | G01C 21/165 |
| | | | | 702/141 |
| 8,645,093 | B2 * | 2/2014 | Brunner | G01R 33/0035 |
| | | | | 324/245 |
| 8,683,707 | B1 * | 4/2014 | Horton, Jr. | G01C 21/165 |
| | | | | 33/355 R |
| 8,749,231 | B2 | 6/2014 | Taylor et al. | |
| 9,319,042 | B2 * | 4/2016 | Thiara | H03K 17/0822 |
| 9,354,343 | B2 * | 5/2016 | Roberts | G01V 1/003 |
| 9,500,464 | B2 * | 11/2016 | Coza | G01B 7/003 |
| 9,506,755 | B2 * | 11/2016 | Tu | G01C 17/38 |
| 2007/0018606 | A1 * | 1/2007 | Iura | H02P 21/141 |
| | | | | 318/807 |
| 2013/0009636 | A1 * | 1/2013 | Figaro | G01R 33/0035 |
| | | | | 324/252 |
| 2014/0316305 | A1 * | 10/2014 | Venkatraman | A61B 5/1112 |
| | | | | 600/595 |

* cited by examiner

Magnetic field vector measured during calibration rotations showing measured points with distortions caused by HI & SI, Mmeas (dots). 410

Undistorted measured magnetic field points, Mfield (circles)
Magnetometer points distorted with HI & SI, Mmeas (dots)
Corrected magnetometer points, Mcal (x's). 420

```
┌─────────────────────────────────────────────────────────────────────┐
│   Measuring, by a magnetic sensor, successive magnetic vectors of a magnetic field │
│                                    610                              │
└─────────────────────────────────────────────────────────────────────┘
                                    │
                                    ▼
┌─────────────────────────────────────────────────────────────────────┐
│   Comparing an angular rotation between successive new measurements and │
│ angular rotation of gyro measurement, and comparing angular rotation between │
│  successive prior measurements and angular rotation of gyro measurement, and │
│   determining if the new measurements more closely match the gyro measurement │
│                                    620                              │
└─────────────────────────────────────────────────────────────────────┘
                                    │
                                    ▼
┌─────────────────────────────────────────────────────────────────────┐
│    Comparing a difference of magnetic magnitude of successive measurements │
│   using newly calculated hard iron and soft iron coefficients, with a difference of │
│      magnetic magnitude of successive measurements using previously calculated │
│ hard iron and soft iron coefficients, and determining if a magnitude difference for │
│ the newly calculated hard iron and soft iron coefficients is less than a magnitude │
│        difference for the previously calculated hard iron and soft iron coefficient 6 │
│                                    630                              │
└─────────────────────────────────────────────────────────────────────┘
                                    │
                                    ▼
┌─────────────────────────────────────────────────────────────────────┐
│  Updating magnetic coefficients of an adaptive filter with new coefficients if a │
│    difference based on the newly calculated hard iron and soft iron coefficients │
│                      more closely match, and differ by less         │
│                                    640                              │
└─────────────────────────────────────────────────────────────────────┘
```

FIGURE 6

AUTOMATICALLY UPDATING HARD IRON AND SOFT IRON COEFFICIENTS OF A MAGNETIC SENSOR

RELATED APPLICATIONS

This patent application claims priority to U.S. Provisional Patent Application Ser. No. 61/943,413, filed Feb. 23, 2014, which is herein incorporated by reference.

FIELD OF THE EMBODIMENTS

The described embodiments relate generally to estimating an orientation. More particularly, the described embodiments relate to apparatuses, methods and systems for automatically updating hard-iron and soft-iron coefficients of a magnetic sensor.

BACKGROUND

Magnetic sensors are used to provide absolute azimuth reference in electronic compassing and motion sensor fusion systems. Specifically, in motion sensor fusion systems, the magnetic sensors can be used for the dual purposes of providing the azimuth reference as well as to provide gyroscope bias and scale error corrections. The inherent advantages of a magnetic sensor are that it is non-inertial and can therefore respond instantaneously to motions without overshoot, or errors caused by linear or angular accelerations. However, their disadvantage is that they are easily perturbed by magnetic distortions from both within a device's frame as well as external to it.

Magnetic distortions within a device's frame consist of hard-iron and soft-iron distortions. Hard-iron distortions are offsets to the magnetic measurements while soft-iron distortions change the gains and phases of the magnetic measurements as a function of rotation of the device within the measurement environment. It is necessary to compute both hard-iron and soft-iron distortions and correct for them in order to measure the magnetic field external to the device accurately so that the measured magnetic field vector can be suitably used in either electronic compassing or motion sensor fusion systems. However, hard-iron and soft-iron distortions change frequently over time and with device configuration changes. Such changes contribute to large errors in electronic compassing and motion sensor fusion systems, and need to be rapidly and automatically corrected as they occur. This necessitates a method to automatically calibrate for changing distortions, and more ideally, done so as a background process of the device during normal usage so that no pre-determined calibration procedure is necessary, thus not causing any discontinuity of accuracy or reliability during use. Such an automated calibration method is challenging to implement properly in most typical magnetic environments due to additional external distortions such as magnetic gradients and anomalies. Automatic calibration methods that currently exist will change their hard-iron and soft-iron coefficient calculations when externally generated distortions are presented to the device, thus often causing significant and unpredictable inaccuracies. The present invention teaches a method to accurately compute a device's hard-iron and soft-iron correction coefficients while properly rejecting magnetic distortions external to the device that would normally cause the inaccurate computations of these coefficients while running continuously as an automated background process.

It is desirable to have apparatuses, methods, and systems for automatically updating hard-iron and soft-iron coefficients of a magnetic sensor.

SUMMARY

An embodiment includes a method for automatically updating hard-iron and soft-iron coefficients of a magnetic sensor of a device. The method includes making measurements of a magnetic field by the magnetic sensor during rotations of the device, determining by at least a criterion whether to input the measurements of the magnetic field into a coefficient estimator, calculating, by the coefficient estimator, new hard iron and soft iron coefficients upon receiving the measurements of the magnetic field, determining a quality of the newly calculated hard iron and soft iron calculated coefficients, and updating existing hard iron and soft iron coefficients to the newly calculated hard iron and soft iron coefficients only if the quality of the newly calculated hard iron and soft iron coefficients is better than a quality of the existing hard iron and soft iron coefficients.

Another embodiment includes a system. The system includes a magnetic sensor operative to make measurements of a magnetic field during rotations of a device, and electronic control circuitry. The electronic control circuitry is operative to determine by at least a criterion whether to input the measurements into a coefficient estimator to generate a new hard iron and soft iron coefficient calculation, calculate a quality of the new hard iron and soft iron coefficients, update existing hard iron and soft iron coefficients to the newly calculated hard iron and soft iron coefficients only if the quality of the newly calculated hard iron and soft iron coefficients is better than a quality of the existing hard iron and soft iron coefficients.

An embodiment includes a method of automatically updating coefficients of a magnetic sensor input to a Kalman filter of a device. The method includes sensing, by a magnetic sensor, a magnetic vector of an ambient magnetic field, tracking motion of the magnetic vector, wherein a tip of the magnetic vector traces to a surface of an ellipsoid, detecting whether the tip is tracing a new surface area of the ellipsoid, wherein a new surface area has not been previously traced, detecting whether the tip trace moves more than a predetermined minimum angular rotation, and recording a certain number of magnetic measurements while the tip is tracing the new surface area and moving more than the a predetermined minimum angular rotation. For each new magnetic measurement, the method includes comparing angular rotation between successive new measurements and an angular rotation of a gyroscope measurement, and comparing angular rotation between successive prior measurements and angular rotation of the gyroscope measurement, and determine if the new magnetic measurements more closely match the gyroscope measurement, and comparing a difference of a magnetic magnitude of successive measurements using newly calculated hard iron and soft iron coefficients, with a difference of magnetic magnitude of successive measurements using the previously calculated hard iron and soft iron coefficients, and determining if a magnitude difference for the newly calculated hard iron and soft iron coefficients is less than a magnitude difference for the previous calculated hard iron and soft iron coefficients. Further, the method includes updating magnetic coefficients of the Kalman filter with the newly calculated hard iron and soft iron coefficients if the difference based on the newly calculated hard iron and soft iron coefficients more closely match, and differ by less.

An embodiment includes a method of tracking a magnetic field. The method includes measuring, by a magnetic sensor, successive magnetic vectors of a magnetic field, comparing an angular rotation between successive new measurements and angular rotation of gyro measurement, and comparing angular rotation between successive prior measurements and angular rotation of gyro measurement, and determining if the new measurements more closely match the gyro measurement, comparing a difference of magnetic magnitude of successive measurements using newly calculated hard iron and soft iron coefficients, with a difference of magnetic magnitude of successive measurements using previously calculated hard iron and soft iron coefficients, and determining if a magnitude difference for the newly calculated hard iron and soft iron coefficients is less than a magnitude difference for the previously calculated hard iron and soft iron coefficients, and updating magnetic coefficients of an adaptive filter with new coefficients if a difference based on the newly calculated hard iron and soft iron coefficients more closely match, and differ by less.

Other aspects and advantages of the described embodiments will become apparent from the following detailed description, taken in conjunction with the accompanying drawings, illustrating by way of example the principles of the described embodiments.

BRIEF DESCRIPTION OF THE DRAWINGS

FIG. 6 is a flow chart that includes steps of a method of tracking a magnetic field, according to an embodiment.

DETAILED DESCRIPTION

Figure 1:
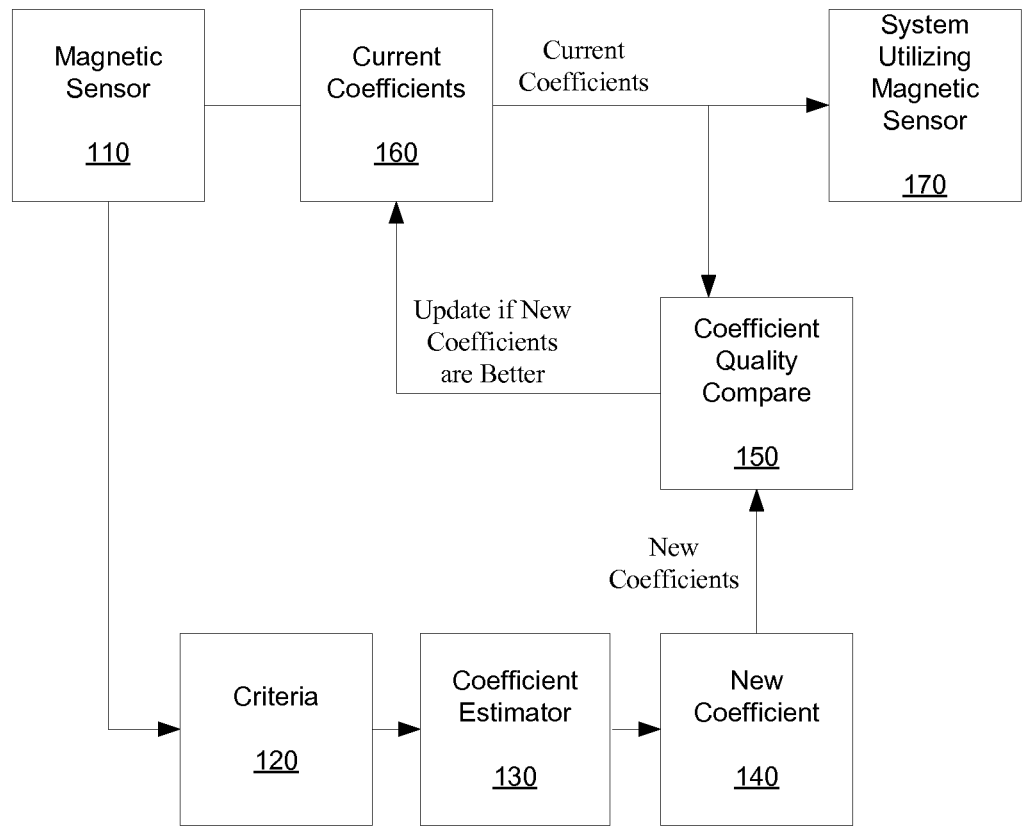
FIG. 1 shows a block diagram of an apparatus or system for automatically updating hard-iron and soft-iron coefficients of a magnetic sensor, according to an embodiment.

The described embodiments provide for apparatuses, methods, and systems for automatically updating hard-iron and soft-iron coefficients of a magnetic sensor. For an embodiment, new coefficients are opportunistically calculated or determined during arbitrary motion of an apparatus or device that includes the magnetic sensor. For an embodiment, the newly calculated coefficients are compared with existing coefficients. If the new coefficients are determined to be better than the existing coefficients, the existing coefficients are replaced with the new coefficients.

Magnetic sensors (magnetometers) are devices used to measure magnetization of a magnetic material, or to measure the strength and, in some cases, the direction of the magnetic field at a point in space.

Hard-Iron Offset

A hard-iron offset of a magnetic sensor results from permanently magnetized ferromagnetic components and structures that are in and around the measurement radius of the magnetic sensor. Generally, the magnetic sensor and the device associated with the magnetic sensor rotate together and the hard-iron offset is a simple vector that adds to or subtracts from the reading of the magnetic sensor.

Soft-Iron Offset

A soft-iron distortion is an interfering magnetic field induced by the geomagnetic field's amplification, attenuation or phase shifting inherent to normally un-magnetized ferromagnetic components of the device that are in and around the measurement radius of the magnetic sensor. Generally, the magnetic sensor and the device associated with the magnetic sensor rotate together and the soft-iron distortion is a gain factor that increases or decreases the reading of the magnetic sensor based upon the strength of the field to be measured. The soft-iron distortion also creates resulting phase errors as well.

Hard-Iron and Soft-Iron Distortions

Distortions of the earth's magnetic field are a result of external magnetic influences generally classified as either a hard-iron or soft-iron effect. If no distorting effects are present, rotating a magnetic sensor through a minimum of 360° and plotting the resulting data as y-axis vs. x-axis measurements results in a circle with its center located at the origin (0, 0). More generally, rotating the magnetic sensor in a spherical fashion in an x, y and z coordinate system results in a sphere centered about about the origin (0, 0, 0).

However, the presence of hard-iron and/or soft-iron effects may produce perturbations of the circle or sphere as a simple offset from the origin in the case of a hard-iron effect, or deform the circle or sphere to produce an ellipse or ellipsoid in the case of a soft-iron effect. It is also possible that both effects are exhibited simultaneously, and this is the case most frequently encountered.

Mathematically, soft iron (SI) and hard iron (HI) cause distortions in the measured magnetic field as:

$$M\text{meas}=((SI^T)*(M\text{field}^T+HI^T))^T$$

where:

SI=[s11 s12 s13 s21 s22 s23 s31 s32 s33]

HI=[h1 h2 h3]

Mfield=[mx my mz]

Once the SI and HI coefficients have been solved in a system, the SI and HI coefficients can be corrected by applying the coefficients:

$$M\text{cal}=SI*(M\text{meas}^T-HI^T)$$

Hard-Iron Distortion

Hard-iron distortion is produced by materials that exhibit a constant, additive field to the earth's magnetic field, thereby generating a constant additive value to the output of each of the magnetometer axes. A speaker magnet, for example, produces a hard-iron distortion. As long as the orientation and position of the magnet relative to the sensor is constant the field and associated offsets will also be constant. A hard-iron distortion can be visibly identified by an offset of the origin of an ideal circle or sphere.

Compensating for hard-iron distortion can be straightforward, accomplished by determining the x, y, and z offsets and then applying these constants directly to the data in the form of an addition or subtraction.

Hard-iron corrections are typically determined by rotating the sensor through a minimum of 360° in a two-dimensional case, and then in another 360° within a plane that is not co-planar to the first in a three-dimensional case, then determining the distance from the center of the circle or sphere to the origin by identifying the average of the maximum and minimum values for each of the axes.

The offsets are then subtracted from the raw x, y and z magnetometer data, thereby largely eliminating the hard-iron distortion. Hard-iron effects within the device frame are constant regardless of orientation or position of the sensing platform. These constant offsets can be stored once calculated and subtracted from the raw magnetometer data. However, hard-iron distortions are frequently changing rapidly over time due to charging and dis-charging of the magnetizing forces inherent to the hard-iron material as well as due to changes in ambient temperature. Thus, although hard-iron distortions appear simple to identify and correct for, they must be corrected for frequently and often in environments that contain external fields that exhibit gradient characteristics so that 360° rotations result in mis-characterizations of the average of the maximum and minimum values for each of the axes.

Soft-Iron Distortion

Unlike hard-iron distortion where the magnetic field is additive to the earth's field, soft-iron distortion is the result of material that influences, or distorts, a magnetic field—but does not necessarily generate a magnetic field itself, and is therefore not additive. Annealed iron, for example, generates a soft-iron distortion. While hard-iron distortion is constant regardless of orientation, the distortion produced by soft-iron materials is dependent upon the orientation of the material relative to the sensor and the magnetic field. Therefore, soft-iron distortion cannot be compensated with a simple constant; instead, a more complicated procedure is required. A soft-iron distortion is typically exhibited as a perturbation of the ideal circle into an ellipse or ellipsoid.

Compensating for soft-iron distortion is generally more compute-intensive than compensating for hard-iron distortion, and it may be more effective from a cost and efficiency perspective—particularly if designing or implementing an embedded system—to eliminate the soft-iron material(s) from the proximity of the sensor. In many cases this is not an option, and implementing a soft-iron compensation method is required.

FIG. 1 shows a block diagram of an apparatus or system for automatically updating hard iron and soft iron coefficients of a magnetic sensor, according to an embodiment. A magnetic sensor 110 senses a magnetic field. For an embodiment, the magnetic sensor 110 opportunistically measures magnetic fields at orientations of the device in which the magnetic sensor is located. For another embodiment, the motions of the device are selected or controlled.

After measuring the magnetic fields, a criterion 120 is checked to determine whether to calculate new hard-iron and soft-iron coefficients. An embodiment of the criterion 120 is to use orientation measurements, such as derived from a magnetometer and accelerometer, or from gyro angular measurements, as the device is rotated in space to track the specific portions of a surface of a sphere that the tip of a vector, which can be a unit vector, traces along the surface of a sphere. Each time the tip of the vector traces a new portion of the surface of the sphere, a magnetic sensor measurement is made and the results stored into memory. When a minimum number of measurement samples of unique portions of the surface area of the traced sphere are recorded, the equation of an ellipsoid generated by the corresponding magnetic sensor measurements is solved to fit a sphere that these magnetic measurements would have made if correct hard-iron and soft-iron coefficients had been applied. The eccentricity and rotation of the magnetically measured ellipsoid is solved to produce correcting soft-iron coefficients and an offset of the center of the magnetically measured ellipsoid from the origin is solved to produce correcting hard-iron coefficients. A further embodiment of criterion 120 is to set a minimum number of unique magnetic sensor measurements to be made before solving for an ellipsoid. A further embodiment of criterion 120 is to define a minimum rotational separation determined by the orientation measurements between each magnetic sensor measurement. A further embodiment is to define a minimum number of magnetic sensor measurements at each unique point on the sphere (groups) to be filtered or averaged in order to reduce errors produced by measurement noise.

A coefficient estimator 130 calculates new coefficients 140 based on the most recently measured magnetic fields that meet the criterion 120. An embodiment of the coefficient estimator 130 is to define the criterion 120 to select magnetic sensor measurement points that represent the minimum and maximum points on each of the X, Y and Z axes of a sphere. The averaged value of the X minimum and maximum is the X hard-iron offset, the averaged value of the Y minimum and maximum is the Y hard-iron offset, the averaged value of the Z minimum and maximum value is the Z hard-iron offset. The inverse of the average of the differences of the X, Y and Z minima and maxima, each respectively divided by two, yields the gain value to multiply magnetic sensor measurement values made from each of the respective X, Y and Z magnetic sensor axes. The offset correction is made first and the gain correction thereafter. A further embodiment of the coefficient estimator 130 is to apply a recursive least squares estimator to the most recently measured magnetic fields that meet the criterion 120, wherein the criterion 120 is set to determine a minimum number of points within a group and the criterion 120 is set to determine a minimum number of groups to record with a minimum angular rotation separation between each group determined by the orientation measurement. For an embodiment, the coefficient estimator 130 includes a Kalman filter recursive estimator, similar to the recursive least squares estimator (note that this is different than the Kalman filter 270 of FIG. 2). The recursive least squares estimator is operative to generate the coefficients to populate the 3×1 hard-iron matrix and the 3×3 soft-iron matrix, including the rotational solution of the ellipsoid to sphere fit to populate the cross axis terms of the 3×3 soft-iron matrix.

The newly calculated coefficients 150 are then compared with the present or previously calculated coefficients (160). If determined to be better than the present coefficients, the present coefficients are updated with the newly calculated coefficients. And if the newly calculated coefficients are determined not to be better than the present coefficients, then the present coefficients are not replaced. An embodiment of determining the quality of the newly calculated hard-iron and soft-iron coefficients is to measure an angular rotation by a gyro and taking successive magnetic sensor measurements that define a magnetic vector that is rotating simultaneously through the gyro measured rotation angle, applying the existing hard-iron and soft-iron coefficients to the successive magnetic sensor measurements to generate a first magnetically based rotation calculation and then applying the newly calculated hard-iron and soft-iron coefficients to the same set of successive magnetic sensor measurements to generate a second magnetically based rotation calculation and comparing the first and second magnetically calculated rotations to select the magnetically based rotation that most closely matches the angular rotation measured by the gyro. A further embodiment is to operate 150 simultaneously to the other parts and activities of the system.

At least some embodiments include additional quality metrics. Such metrics can include, for example, observations of the corrected magnetometer magnitude over a range of orientation changes—the more constant the magnitude, the better the correction, observation of the stability of the estimated coefficients, and/or observation of the stability of the dip angle (angle between magnetic sensor and acceleration sensor vectors) over orientation changes.

The present hard iron and soft iron coefficients are stored (160) for use by a system 170.

Figure 2:
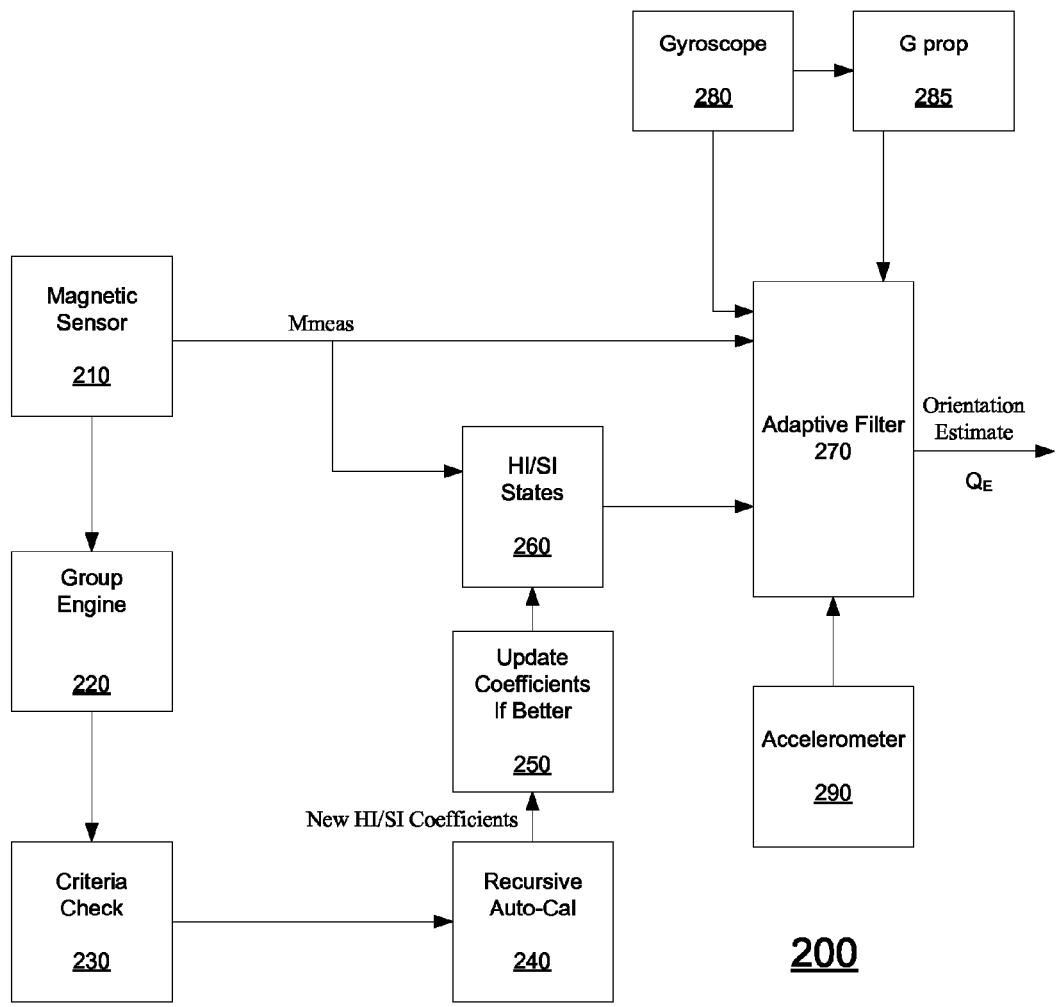
FIG. 2 shows a block diagram of an orientation and/or motion detection system that includes automatic updating of hard-iron and soft-iron coefficients of a magnetic sensor of the system, according to another embodiment.

FIG. 2 shows a block diagram of an orientation and/or motion detection system 200 that includes automatic updating of hard iron and soft iron coefficients of a magnetic sensor 210 of the system 200, according to another embodiment. The system 200 includes an adaptive filter 270 (for an embodiment, the adaptive filter includes a Kalman filter) that receives hard-iron and soft-iron coefficients generated by the magnetic sensor 210, and the adaptive filter further receives a sensed acceleration signal from an accelerometer 290, and a sensed signal from a gyroscope 280. Based on the received magnetic, acceleration and gyroscope signals, the adaptive filter 270 generates an estimated orientation (Q) of the device or apparatus that includes the magnetic sensor 210, the accelerometer 290 and the gyroscope 280.

As shown, a group engine 220 receives a plurality of magnetic signal measurements from the magnetic sensor 210. For an embodiment, the measurements includes measuring a magnetic vector associated with the magnetic field, and further includes tracking motion of the magnetic vector during device rotation.

Criteria (shown as criteria check block 230), as will be described, are to be satisfied before recording the magnetic signal measurements. Visually, the magnetic vector traces a surface of an ellipsoid. For an embodiment, the criterion includes detecting that the magnetic vector traces the surface of the ellipsoid not traced since a prior hard iron and soft iron calculated coefficient update. Further, for an embodiment, the criteria include determining that the magnetic vector has moved more than a predetermined minimum displacement along the surface of the ellipsoid. For an embodiment, the criterion includes detecting that the magnetic vector traces the surface of the ellipsoid not traced since a predetermined period of time, and determining that the magnetic vector has moved more than a predetermined minimum displacement along the surface of the ellipsoid.

Once measured, and the criteria satisfied, the magnetometer data from the group engine 220 are input into the recursive autocal block (240), which continually calculates new hard-iron and soft-iron coefficients. A compare block 250 then compares the newly calculated hard iron and soft iron coefficients to determine which of them has a higher level of quality. That is, an embodiment includes determining the quality of the newly calculated hard-iron and soft-iron coefficients and only updating existing hard-iron and soft-iron coefficients to the newly calculated hard-iron and soft-iron coefficients if the quality of the newly calculated hard-iron and soft-iron coefficients is better than a quality of existing hard-iron and soft-iron coefficients. For an embodiment, determining whether the newly calculated coefficients are better quality than the previously calculated coefficients includes comparing angular rotation between successive new measurements and angular rotation of gyro measurements, and comparing angular rotation between successive prior measurements and angular rotation of a gyro measurement, and determining if the new measurements more closely match the gyro measurement than the successive prior measurements. That is, measurements from the gyroscope 230 are compared with angular rotations of successive new measurements and successive prior measurements. The one of the two that matches the angular rotations of the gyroscope measurements is selected as having the better quality.

Further, for an embodiment, determining whether the newly calculated coefficients are better quality than the previously calculated coefficients includes comparing a difference of magnetic magnitudes of successive new measurements with a difference of magnetic magnitudes of successive old measurements, and determining if the successive new measurements differ by less than the successive old measurements.

If the newly calculated coefficients are determined to be of higher quality, the newer coefficients replace the prior coefficients as the current or actively used coefficients. The updated, current coefficients are stored in HI/SI states block 260. Further, the current HI/SI coefficients are utilized by the adaptive filter 270.

A gyroscope prop 285 provides the angular rotational measurement references necessary to implement the described embodiments.

As previously stated, the sensed signals of the magnetic sensor 210 (coefficients), the accelerometer 290 and the gyroscope 280 are received by an adaptive filter 270. Based on the received sensed signals, the adaptive filter 270 generates the orientation estimate (Q) of the device. The orientation estimate (Q) includes a Quaternion. Quaternions, also known as versors, provide a convenient mathematical notation for representing orientations and rotations of objects in three dimensions.

As previously stated, for an embodiment, the adaptive filter 270 includes a Kalman filter.

Kalman Filters

For an embodiment, the Kalman filter, includes a series of measurements observed over time, containing noise (random variations) and other inaccuracies, and produces estimates of unknown variables that tend to be more precise than those based on a single measurement alone. More formally, the Kalman filter operates recursively on streams of noisy input data to produce a statistically optimal estimate of the underlying system state. The Kalman filter has numerous applications in technology. A common application is for guidance, navigation and control of vehicles, particularly aircraft and spacecraft.

For an embodiment, the Kalman filter produces estimates of the current state variables, along with their uncertainties. Once the outcome of the next measurement (necessarily corrupted with some amount of error, including random noise) is observed, these estimates are updated using a weighted average, with more weight being given to estimates with higher certainty. Because of the Kalman filter's recursive nature, it can run in real time using only the present input measurements and the previously calculated state and its uncertainty matrix, while no additional past information is required.

Figure 3:
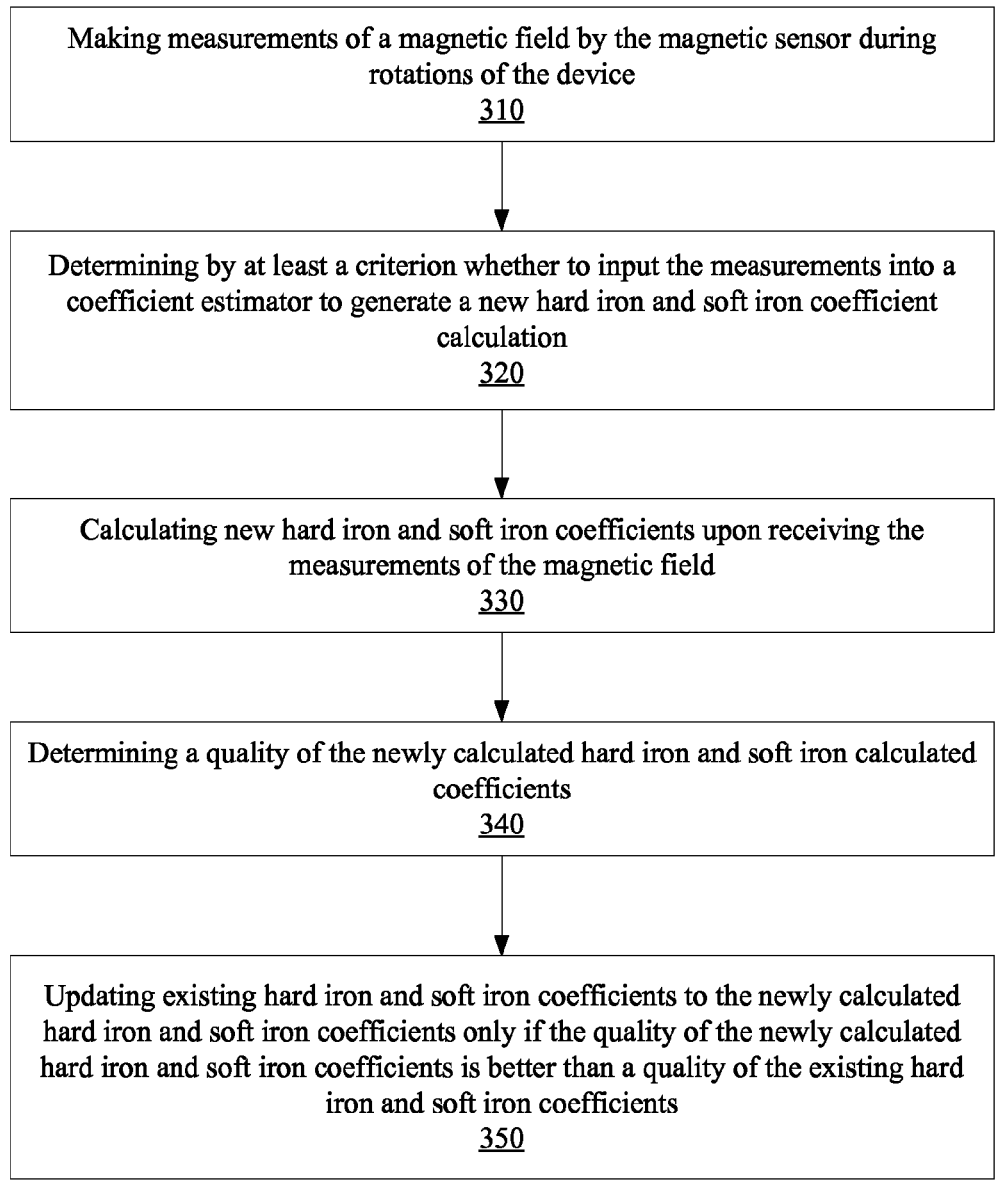
FIG. 3 shows is a flow chart that includes steps of a method of automatically updating hard-iron and soft-iron coefficients of a magnetic sensor of a device, according to an embodiment.

FIG. 3 shows is a flow chart that includes steps of a method of automatically updating hard iron and soft iron coefficients of a magnetic sensor of a device, according to an embodiment. A first step 310 includes making measurements of a magnetic field by the magnetic sensor during rotations of the device. A second step 320 includes determining by at least a criterion whether to input the measurements of the magnetic field into a coefficient estimator. A third step 330 includes calculating, by the coefficient estimator, new hard iron and soft iron coefficients upon receiving the measurements of the magnetic field. A fourth step 340 includes determining a quality of the newly calculated hard iron and soft iron calculated coefficients. A fifth step 350 includes updating existing hard iron and soft iron coefficients to the newly calculated hard iron and soft iron coefficients only if (or upon, or after determining) the quality of the newly calculated hard iron and soft iron coefficients is better than a quality of the existing hard iron and soft iron coefficients.

For an embodiment, the rotations of the device are arbitrary. For an embodiment, the measurements are opportunistically made depending upon the arbitrary rotations.

At least some embodiments further include making additional measurements of the magnetic field for updating of the newly calculated hard iron and soft iron coefficients. For an embodiment, the coefficient estimator operates recursively.

For an embodiment, the measurements include measuring a magnetic vector associated with the magnetic field, and further comprising tracking motion of the magnetic vector. For an embodiment, the magnetic vector traces a surface of an ellipsoid, and wherein determining by at least the criterion comprises detecting that the magnetic vector traces the surface of the ellipsoid not traced since a prior hard iron and soft iron calculated coefficient update, and determining that the magnetic vector has moved more than a predetermined minimum displacement along the surface of the ellipsoid. For an embodiment, the magnetic vector traces a surface of an ellipsoid, and wherein determining by at least the criterion comprises detecting that the magnetic vector traces the surface of the ellipsoid not traced since a predetermined period of time, and determining that the magnetic vector has moved more than a predetermined minimum displacement along the surface of the ellipsoid.

Generally, a tradeoff exists between noise and how often or quickly updates occur. A number of samples per group are selectable, wherein a group includes a particular section of the surface of the ellipsoid. For at least some embodiments, a size of the surface section for each group is also selectable.

At least some embodiments further include determining the quality of the newly calculated hard iron and soft iron coefficients and only updating existing hard iron and soft iron coefficients to the newly calculated hard iron and soft iron coefficients if the quality of the newly calculated hard iron and soft iron coefficients is better than a quality of existing hard iron and soft iron coefficients. For an embodiment, this process includes measuring an angular rotation by a gyro, taking successive magnetic sensor measurements simultaneously with the angular rotation as measured by the gyro, applying the existing hard and soft iron coefficients to the successive magnetic sensor measurements to generate a first rotation calculation, applying the newly calculated hard and soft iron coefficients to the successive magnetic sensor measurements to generate a second rotation calculation, comparing the first calculated rotation and the second calculated rotation to angular rotation measured by the gyro, and selecting the one of the first calculated and the second calculated rotation most closely matches the angular rotation measured by the gyro.

For an embodiment, if the new measurements more closely match the angular rotation measured by the gyro, then the existing hard iron and soft iron coefficients are updated with the new measurements.

For an embodiment, determining the quality of the newly calculated hard iron and soft iron coefficients additionally includes comparing a difference of magnetic magnitude of successive measurements using the newly calculated hard iron and soft iron coefficients, with a difference of magnetic magnitude of successive measurements using the existing hard iron and soft iron coefficients, determining if the magnetic magnitude difference for the newly calculated hard iron and soft iron coefficients is less than the magnetic magnitude difference for the existing hard iron and soft iron coefficients, and selecting either the newly calculated hard iron and soft iron coefficients or the existing hard iron and soft iron coefficients, depending on which results in a smallest magnitude difference over successive measurements.

For an embodiment, a sensed output of the magnetic sensor is received by an adaptive filter, and wherein the newly calculated hard and soft iron coefficients are updated within the adaptive filter.

Figure 4:
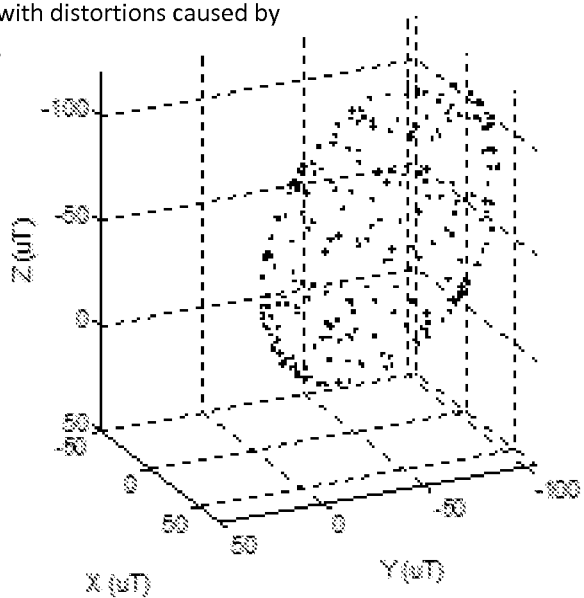
FIG. 4 shows a visual depiction of a magnetic vector sensed by a magnetic sensor during calibration of hard-iron and soft-iron coefficients of a magnetic sensor, according to an embodiment.
Figure 4:
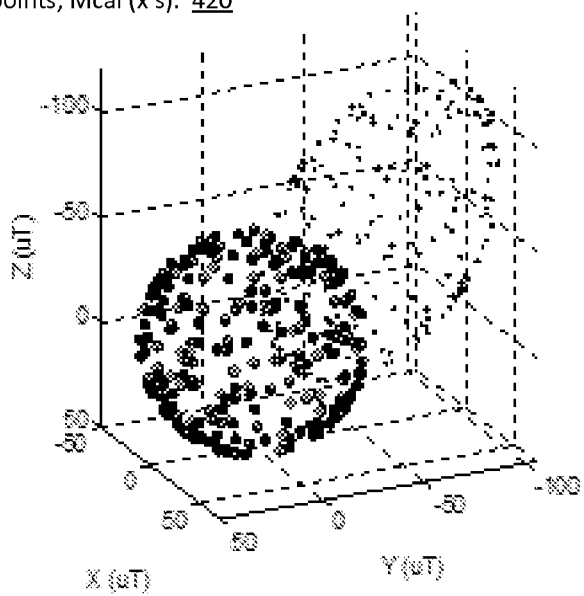

FIG. 4 shows a visual depiction of a magnetic field vector sensed by a magnetic sensor during calibration of hard iron and soft iron coefficients of a magnetic sensor, according to an embodiment. The measured field points Mmeas during the calibration rotations are distorted by hard iron (HI) and soft iron (SI), as seen in 410. The corrected magnetometer points Mcal are shown in 420, after the coefficients HI & SI have been determined and applied to the points Mmeas. The ellipsoid shape of the SI & HI distorted sphere is apparent. After SI & HI coefficients are learned, the corrected measurements make the shape of a sphere instead of an ellipsoid (420).

The SI & HI distortions on the underlying field result in the distorted plot of Mmeas (dots) 410.

$$M\text{meas}=((SI^T)*(M\text{field}^T+HI^T))^T$$

SI & HI shown in 410:
SI=[0.998 0.0405 0.0512 0.0317 1.07−0.210 0.0607−0.257 0.784]
HI=[19.7−53.6−52.0] (uT)

The corrected points Mcal (x's) are shown in 420, and can be calculated from the SI & HI coefficients.

$$M\text{cal}=(SI*(M\text{meas}^T-HI^T))^T$$

Figure 5:
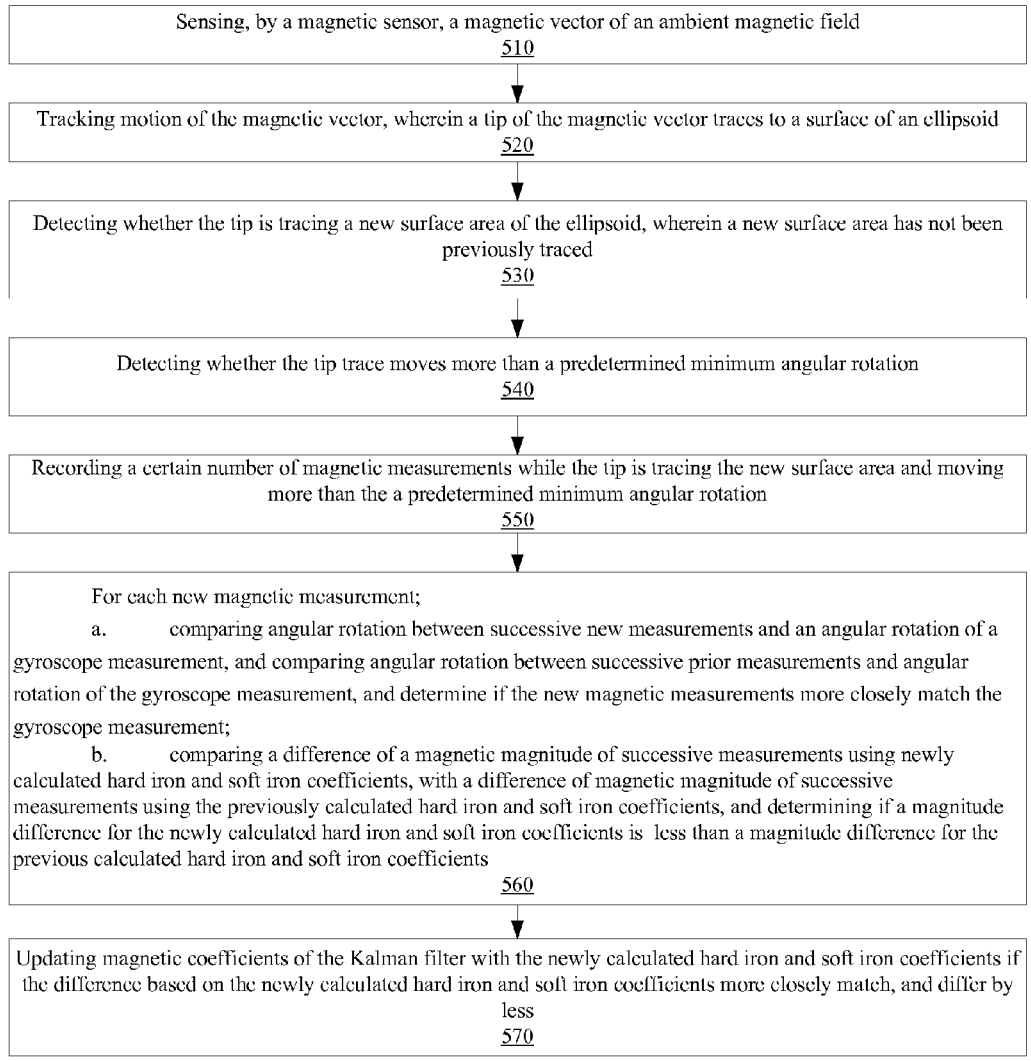
FIG. 5 is a flow chart that includes steps of a method of automatically updating coefficients of a magnetic sensor input to a Kalman filter of a device, according to an embodiment.

FIG. 5 is a flow chart that includes steps of a method of automatically updating coefficients of a magnetic sensor input to a Kalman filter of a device, according to an embodiment. The steps of the flow chart include various of the previously described embodiments. A first step 510 includes sensing, by a magnetic sensor, a magnetic vector of an ambient magnetic field. A second step 520 includes tracking motion of the magnetic vector, wherein a tip of the magnetic vector traces to a surface of an ellipsoid. A third step 530 includes detecting whether the tip is tracing a new surface area of the ellipsoid, wherein a new surface area has not been previously traced. A fourth step 540 includes detecting whether the tip trace moves more than a predetermined minimum angular rotation. A fifth step 550 includes recording a certain number of magnetic measurements while the tip is tracing the new surface area and moving more than a predetermined minimum angular rotation. A sixth step 560 includes for each new magnetic measurement (a) comparing angular rotation between successive new measurements and an angular rotation of a gyroscope measurement, and comparing angular rotation between successive prior measurements and angular rotation of the gyroscope measurement, and determine if the new magnetic measurements more closely match the gyroscope measurement, and (b) comparing a difference of a magnetic magnitude of successive measurements using newly calculated hard iron and soft iron coefficients, with a difference of magnetic magnitude of successive measurements using the previously calculated hard iron and soft iron coefficients, and determining if a magnitude difference for the newly calculated hard iron and soft iron coefficients is less than a magnitude difference for the previous calculated hard iron and soft iron coefficients. A seventh step 570 includes updating magnetic coefficients of the Kalman filter with the newly calculated hard iron and soft iron coefficients if the difference based on the newly calculated hard iron and soft iron coefficients more closely match, and differ by less.

FIG. 6 is a flow chart that includes steps of a method of tracking a magnetic field, according to an embodiment. The steps of the flow chart include various of the previously described embodiments. These steps incorporate the previously described embodiments in varying configurations. A first step 610 includes measuring, by a magnetic sensor, successive magnetic vectors of a magnetic field. A second step 620 includes comparing an angular rotation between successive new measurements and angular rotation of gyro measurement, and comparing angular rotation between successive prior measurements and angular rotation of gyro measurement, and determining if the new measurements more closely match the gyro measurement. A third step 630 includes comparing a difference of magnetic magnitude of successive measurements using newly calculated hard iron and soft iron coefficients, with a difference of magnetic magnitude of successive measurements using previously calculated hard iron and soft iron coefficients, and determining if a magnitude difference for the newly calculated hard iron and soft iron coefficients is less than a magnitude difference for the previously calculated hard iron and soft iron coefficients. A fourth step 640 includes updating magnetic coefficients of an adaptive filter with new coefficients if a difference based on the newly calculated hard iron and soft iron coefficients more closely match, and differ by less.

Although specific embodiments have been described and illustrated, the described embodiments are not to be limited to the specific forms or arrangements of parts so described and illustrated. The embodiments are limited only by the appended claims.

What is claimed:

1. A method of automatically updating hard iron and soft iron coefficients of a magnetic sensor of a device, comprising:
   measuring, by the magnetic sensor, a magnetic field during rotations of the device;
   determining by at least a criterion whether to input the measurements of the magnetic field into a coefficient estimator;
   calculating, by the coefficient estimator, new hard iron and soft iron coefficients upon receiving the measurements of the magnetic field;
   measuring an angular rotation by a gyro;
   successively measuring the magnetic field, by the magnetic sensor, while simultaneously measuring the angular rotation by the gyro, comprising:
      measuring the magnetic field while applying the existing hard and soft iron coefficients to the successive magnetic sensor measurements to generate a first rotation calculation;
      measuring the magnetic field while applying the newly calculated hard and soft iron coefficients to the successive magnetic sensor measurements to generate a second rotation calculation;
   comparing the first calculated rotation and the second calculated rotation to angular rotation measured by the gyro;
   selecting the one of the first calculated and the second calculated rotation that most closely matches the angular rotation as measured by the gyro; and
   measuring, by the magnetic sensor, the magnetic field by the magnetic sensor during rotations of the device using the newly calculated hard and soft iron coefficients when the second calculated rotation is selected.

2. The method of claim 1, wherein the rotations of the device are arbitrary.

3. The method of claim 2, wherein the measurements are opportunistically made depending upon the arbitrary rotations.

4. The method of claim 1, further comprising making additional measurements of the magnetic field for updating of the newly calculated hard iron and soft iron coefficients.

5. The method of claim 1, wherein the coefficient estimator operates recursively.

6. The method of claim 1, wherein the measurements include measuring a magnetic vector associated with the magnetic field, and further comprising tracking motion of the magnetic vector.

7. The method of claim 6, wherein the magnetic vector traces a surface of an ellipsoid, and wherein determining by at least the criterion comprises detecting that the magnetic vector traces the surface of the ellipsoid not traced since a prior hard iron and soft iron calculated coefficient update, and determining that the magnetic vector has moved more than a predetermined minimum displacement along the surface of the ellipsoid.

8. The method of claim 6, wherein the magnetic vector traces a surface of an ellipsoid, and wherein determining by at least the criterion comprises detecting that the magnetic vector traces the surface of the ellipsoid not traced since a predetermined period of time, and determining that the magnetic vector has moved more than a predetermined minimum displacement along the surface of the ellipsoid.

9. The method of claim 1, wherein if the newly calculated hard iron and soft iron coefficients more closely match the angular rotation measured by the gyro, then updating the existing hard iron and soft iron coefficients.

10. The method of claim 1, wherein determining a quality of the newly calculated hard iron and soft iron coefficients additionally comprises:
    comparing a difference of magnetic magnitude of successive measurements using the newly calculated hard iron and soft iron coefficients, with a difference of magnetic magnitude of successive measurements using the existing hard iron and soft iron coefficients;
    determining if the magnetic magnitude difference for the newly calculated hard iron and soft iron coefficients is less than the magnetic magnitude difference for the existing hard iron and soft iron coefficients;
    selecting either the newly calculated hard iron and soft iron coefficients or the existing hard iron and soft iron coefficients, depending on which results in a smallest magnitude difference over successive measurements.

11. The method of claim 9, wherein a sensed output of the magnetic sensor is received by an adaptive filter, and wherein the newly calculated hard and soft iron coefficients are updated within the adaptive filter.

12. A sensing system that automatically updates hard iron and soft iron coefficients of a magnetic sensor of the system, comprising:
    the magnetic sensor operative to measure a magnetic field during rotations of the device;
    a gyroscope operative to measure an angular rotation;
    electronic control circuitry, the electronic control circuitry operative to:
       determine by at least a criterion whether to input the measurements into a coefficient estimator to generate a new hard iron and soft iron coefficients;
    wherein the magnetic sensor successively measures the magnetic field simultaneously with the the gyroscope measuring the angular rotation;
    wherein the electronic control circuitry is further operative to:
       apply the existing hard and soft iron coefficients to the successive magnetic sensor measurements to generate a first rotation calculation;

apply the newly calculated hard and soft iron coefficients to the successive magnetic sensor measurements to generate a second rotation calculation;

compare the first calculated rotation and the second calculated rotation to angular rotation measured by the gyroscope;

select the one of the first calculated and the second calculated rotation that most closely matches the angular rotation measured by the gyro; and measuring the magnetic field by the magnetic sensor during rotations of the device using the newly calculated hard and soft iron coefficients when the second calculated rotation is selected.

13. The system of claim 12, wherein measuring the magnetic field includes measuring a magnetic vector associated with the magnetic field, and further comprising tracking motion of the magnetic vector.

14. The system of claim 13, wherein the magnetic vector traces a surface of an ellipsoid, and wherein determining by at least the criterion comprises detecting that the magnetic vector traces the surface of the ellipsoid not traced since a prior hard iron and soft iron calculated coefficient update, and determining that the magnetic vector has moved more than a predetermined minimum displacement along the surface of the ellipsoid.

15. The system of claim 13, wherein the magnetic vector traces a surface of an ellipsoid, and wherein determining by at least the criterion comprises detecting that the magnetic vector traces the surface of the ellipsoid not traced since a predetermined period of time, and determining that the magnetic vector has moved more than a predetermined minimum displacement along the surface of the ellipsoid.

16. The system of claim 12, wherein determining the quality of the newly calculated hard iron and soft iron coefficients additionally comprises:

comparing a difference of magnetic magnitude of successive measurements using the newly calculated hard iron and soft iron coefficients, with a difference of magnetic magnitude of successive measurements using existing hard iron and soft iron coefficients;

determining if the magnetic magnitude difference for the newly calculated hard and soft iron coefficients is less than the magnetic magnitude difference for the existing hard iron and soft iron coefficients;

selecting either the newly calculated hard and soft iron coefficients or the existing hard iron and soft iron coefficients, depending on which results in a smallest magnitude difference over successive measurements.

17. A method of automatically updating coefficients of a magnetic sensor input to a Kalman filter of a device, comprising:

sensing, by a magnetic sensor, a magnetic vector of an ambient magnetic field;

sensing, by a gyro, an angular rotation;

tracking motion of the magnetic vector, wherein a tip of the magnetic vector traces to a surface of an ellipsoid;

detecting whether the tip is tracing a new surface area of the ellipsoid, wherein a new surface area has not been previously traced;

detecting whether the tip trace moves more than a predetermined minimum angular rotation;

recording a certain number of magnetic measurements while the tip is tracing the new surface area and moving more than the a predetermined minimum angular rotation;

for each new magnetic measurement;
  a. comparing angular rotation between successive new magnetic measurements and an angular rotation of a gyroscope measurement, and comparing angular rotation between successive prior magnetic measurements and angular rotation of the gyroscope measurement, and determine if the new magnetic measurements more closely match the gyroscope measurement;
  b. comparing a difference of a magnetic magnitude of successive magnetic measurements using newly calculated hard iron and soft iron coefficients, with a difference of magnetic magnitude of successive magnetic measurements using the previously calculated hard iron and soft iron coefficients, and determining if a magnitude difference for the newly calculated hard iron and soft iron coefficients is less than a magnitude difference for the previous calculated hard iron and soft iron coefficients;

updating magnetic coefficients of the Kalman filter with the newly calculated hard iron and soft iron coefficients if the difference based on the newly calculated hard iron and soft iron coefficients more closely match, and differ by less;

generating, by the Kalman filter, an estimated orientation (Q) of the device using the newly calculated hard iron and soft iron coefficients based on the sensed magnetic vector and the sensed angular rotation.

18. A method of tracking a magnetic field, comprising:

measuring, by a magnetic sensor, successive magnetic vectors of a magnetic field;

measuring, by a gyro, an angular rotation;

comparing an angular rotation between successive new magnetic vector measurements and angular rotation measurements and comparing angular rotation between successive prior magnetic vector measurements and angular rotation measurements, and determining if the new magnetic vector measurements more closely match the angular rotation measurements;

comparing a difference of magnetic magnitude of successive magnetic measurements using newly calculated hard iron and soft iron coefficients, with a difference of magnetic magnitude of successive magnetic measurements using previously calculated hard iron and soft iron coefficients, and determining if a magnitude difference for the newly calculated hard iron and soft iron coefficients is less than a magnitude difference for the previously calculated hard iron and soft iron coefficients; and updating magnetic coefficients of an adaptive filter with new coefficients if a difference based on the newly calculated hard iron and soft iron coefficients more closely match, and differ by less;

generating, by the adaptive filter, an estimated orientation (Q) of the device using the newly calculated hard iron and soft iron coefficients based on the sensed magnetic vector and the sensed angular rotation.

* * * * *